(12) United States Patent
Struik et al.

(10) Patent No.: US 12,310,626 B2
(45) Date of Patent: May 27, 2025

(54) EXTERNAL DISTRACTOR AND ADJUSTMENT DEVICE FOR USE IN SUCH A DISTRACTOR

(71) Applicant: ARTHROSAVE HOLDING B.V., Calemborg (NL)

(72) Inventors: Thijmen Struik, Montfoort (NL); Floris Paulus Jacobus Gerardus Lafeber, Houten (NL); Vincent Marianus Cloostermans, Enschede (NL); Karianne Hide Lindenhovius, De Meern (NL)

(73) Assignee: ARTHROSAVE HOLDING B.V., Culemborg (NL)

( * ) Notice: Subject to any disclaimer, the term of this patent is extended or adjusted under 35 U.S.C. 154(b) by 315 days.

(21) Appl. No.: 17/638,032

(22) PCT Filed: Aug. 26, 2019

(86) PCT No.: PCT/EP2019/072715
§ 371 (c)(1),
(2) Date: Feb. 24, 2022

(87) PCT Pub. No.: WO2021/037336
PCT Pub. Date: Mar. 4, 2021

(65) Prior Publication Data
US 2022/0280195 A1  Sep. 8, 2022

(51) Int. Cl.
*A61B 17/64* (2006.01)
*A61B 17/66* (2006.01)

(52) U.S. Cl.
CPC .......... *A61B 17/6458* (2013.01); *A61B 17/66* (2013.01)

(58) Field of Classification Search
CPC ..... A61B 17/6458; A61B 17/66; A61B 17/64; A61B 17/6491
See application file for complete search history.

(56) References Cited

U.S. PATENT DOCUMENTS 6,030,386 A * 2/2000 Taylor ............... A61B 17/62
606/56
8,574,232 B1 * 11/2013 Ross ............... A61B 17/66
606/57

(Continued)

OTHER PUBLICATIONS

International Search Report and Written Opinion for PCT/EP2019/072715, mailed May 18, 2020, ten (10) pages).

*Primary Examiner* — Julianna N Harvey
(74) *Attorney, Agent, or Firm* — MH2 Technology Law Group LLP

(57) ABSTRACT

An external distractor to gradually enlarge the distance between first and second bone parts includes first and a second connection devices. The first and second connection devices are connected to the first and second bone parts, respectively, with first and second respective bone pins. The distractor includes an adjustment device between the connection devices for adjusting the distance between the connection devices along an adjustment axis. The adjustment device includes a tubular base body coupled to the first connection device, an extension tube coupled to the second connection device and an adjustment mechanism for moving the extension tube with respect to the base body along the adjustment axis. The adjustment mechanism includes a rotatable adjustment ring for moving the extension tube upon rotation of the adjustment ring around the adjustment axis. The adjustment mechanism includes a spring engaging the adjustment ring for preventing unintended activation of the adjustment mechanism.

17 Claims, 8 Drawing Sheets

(56) References Cited

U.S. PATENT DOCUMENTS

| | | | |
|---|---|---|---|
| 2015/0272644 A1* | 10/2015 | Noon | A61B 17/8009 606/90 |
| 2015/0305776 A1* | 10/2015 | Ross | A61B 17/60 606/56 |
| 2018/0368887 A1 | 12/2018 | Lauf et al. | |

* cited by examiner

EXTERNAL DISTRACTOR AND ADJUSTMENT DEVICE FOR USE IN SUCH A DISTRACTOR

This application is a national stage filing under 35 U.S.C. 371 of pending International Application No. PCT/EP2019/072715, filed Aug. 26, 2019, the entirety of which application is incorporated by reference herein.

The present invention relates to an external distractor arranged to gradually enlarge the distance between a first bone part and a second bone part, wherein the distractor comprises a first and a second connection device, wherein the first connection device is arranged to be connected to the first bone part with at least one first bone pin and wherein the second connection device is arranged to be connected to the second bone part with at least one second bone pin, wherein the distractor further comprises an adjustment device arranged between the first and second connection devices for adjusting the distance along an adjustment axis, or other properties such as resilience, between the first and the second connection devices, wherein the adjustment device comprises a tubular base body coupled to the first connection device, an extension tube coupled to the second connection device and an adjustment mechanism for moving the extension tube with respect to the base body along the adjustment axis, wherein the adjustment mechanism comprises a rotatable adjustment ring for moving the extension tube upon rotation of the adjustment ring around the adjustment axis.

Such an external distractor is for instance described in WO2017/016611 A1, which is hereby incorporated by reference.

In this known system, two connection devices are coupled to a patient using respective bone pins at a mutual distance, for instance spanning a joint such as the knee. The connection devices are coupled using an adjustment device, and typically one or more ball joints to allow movement between the connection devices, wherein the adjustment device is arranged to increase the distance, preferably in a gradual manner, between the connection devices along the adjustment axis and therewith establishing distraction of a joint. Additional components such as a connection rod may be provided between the connection devices. Such an adjustment device typically comprises a telescopic tube assembly, wherein an extension tube is movable with respect to a tubular base body. Adjustment, i.e. extension, of the extension tube can be achieved by manipulating an adjustment ring. The ring and the extension tube may for instance be provided with cooperating threading such that rotation of the ring leads to movement of the extension tube with respect to the base body along the adjustment axis. The extension tube is preferably aligned with the adjustment axis, which is also aligned with the axis of movement of the two bone parts as mentioned above. An improved distraction process may be obtained when the distraction device comprises a resilient member such as a spring.

It is a goal of the present invention, next to other goals, to provide an improved external distractor—in terms of for instance safety and/or user-friendliness.

This goal, amongst other goals, is met by a method according to appended claim 1. More specifically, this goal, amongst other goals, is met by the above mentioned external distractor wherein the adjustment mechanism further comprises a spring member engaging the adjustment ring. The spring member is preferably arranged for preventing unintended, i.e. accidental, activation of the adjustment mechanism, or preventing adjustment. During distraction, the distance between the connection devices, and thereby for instance the bones comprising a joint, is preferably gradually and incrementally increased. This adjustment is typically done by the the end-user, e.g. a clinician or patient. The adjustment mechanism is manually operable, in specific cases with a dedicated tool or key for adjusting the setting. At the same time, accidental or unintended adjustment during clinical application of the distractor needs to be prevented. The spring member prevents this accidental rotation, such that the safety of the distractor is improved.

The spring member hereby engages the adjustment ring such that accidental rotation of the adjustment ring is prevented. The spring member may for instance be coupled between the adjustment ring and distraction device, for instance the base body thereof, to increase the rotating resistance of the adjustment ring. Rotation of the ring then requires an increased rotational force, e.g. torque, such that activation of the adjustment mechanism due to low rotational forces during common daily activities is prevented. The spring member may for instance be a leaf spring engaging the adjustment ring. Generally, it is preferred if the spring member is arranged to prevent rotation of the adjustment ring.

The spring member may be arranged to increase the rotational force, e.g. torque, needed to rotate the ring, in particular to such an extent that manually operating the ring is not possible. It is then preferred if the ring is arranged to cooperate with a tool for rotating the ring. The ring may for instance be formed partially non-cylindrical, for instance comprising at least one surface to engage with the tool, which may be a wrench. The invention further relates to a combination of a tool and the distractor.

According to a preferred embodiment, the adjustment ring is movable between a locked position, wherein rotation of the ring is prevented, and an unlocked position wherein the ring is rotatable. Rotation of the ring is then only possible when the adjustment ring is in the unlocked position. It is then preferred if the adjustment ring is biased towards the locked position, e.g. by means of the spring member. Upon release of the adjustment ring by the patient, the adjustment ring will then automatically move to the locked position. Preferably, the spring member is arranged to urge the adjustment ring towards the locked position. In a preferred embodiment, the adjustment ring is put into the unlocked position upon exertion of an additional torque to the adjustment ring, for instance provided by a spring member, over the torque required for adjusting the distraction setting.

It is also possible that in the locked position, rotation of the adjustment ring is possible without adjusting or activating the adjustment mechanism. The adjustment ring may for instance be movable between an engaged position, wherein the adjustment ring engages the adjustment mechanism for adjusting e.g. the length upon engagement of the adjustment ring, and a disengaged position wherein the adjustment ring is decoupled from the adjustment mechanism. In the decoupled position, rotation will not lead to activation of the adjustment mechanism. The disengaged position may then correspond to the locked position.

An adjustment mechanism comprising a ring for actuating the adjustment mechanism has advantages in terms of user-friendliness. It is however also possible that the adjustment mechanism has an actuating member other than a ring. For instance, the actuating member may be partly ring shaped or be in the form of a tab, for instance arranged for rotation. Such a tab may for instance be movable to an inward position, wherein the adjustment mechanism can be engaged upon rotation, and an outward position wherein the actuating member is decoupled from the adjustment mechanism. A spring member may for instance urge the actuating member outwardly to the outward or disengaged position. Pushing the actuating member inwardly, preferably against the spring force, then allows adjustment. Two different movements are then simultaneously required for initiating adjustment of the length, one inwardly and one rotating movement. This prevents accidental rotation and thus improves the safety. At the same time, the user only needs to use a single mechanism, i.e. the actuating member, for instance in the form of the adjustment ring. For moving to the inward position of for instance the tab, a tool may be used or may even be necessary.

It is however preferred if the adjustment ring is movable along the adjustment axis between the locked and unlocked positions. For activating the adjustment mechanism, the ring needs to be moved along the adjustment axis first, before the ring can be rotated or more generally before the adjustment mechanism can be activated upon rotation.

According to a further preferred embodiment, the adjustment ring comprises an inner ring member and an outer ring member, wherein the outer ring member is arranged to be engaged by a user. It is for instance possible that the spring member is arranged between the inner and outer member.

Preferably, the inner ring member and outer ring member are coupled such that rotation of the outer ring results in rotation of the inner ring, at least in the unlocked or engaged position as described above. It may be possible that in the locked or disengaged position, the outer ring is freely rotatable with respect to the inner ring, while in the engaged or unlocked position, the inner and outer ring members are coupled for rotating both the inner and the outer ring member.

Preferably, the inner and outer ring members are coupled in a substantially form-locked manner, i.e. having at least complementary shapes, such that rotation of the outer ring member rotates the inner ring member. The inner surface of the outer ring member may thereto be formed at least partially complementary to the outer surfaces of the inner ring member.

Preferably the outer ring member is movable with respect to the inner ring member along the adjustment axis. This intuitive movement improves the user-friendliness.

An efficient movement of the extension tube upon rotation of the adjustment ring is obtained when the ring and the extension tube are provided with cooperating threading. More preferably, the inner ring member and the extension tube are provided with cooperating threading for moving the extension tube upon rotation of the inner ring.

A compact composition which efficiently urges the outer ring towards the unlocked position is obtained when the spring member is arranged between the inner and outer ring member. The spring may be arranged to relatively move the inner and outer ring members along the adjustment axis. Preferably, the spring member is arranged to move the outer ring member relative to the inner ring member and tube.

It is to be noted that the use of a spring member is efficient in moving the adjustment ring towards the locked position. It may also be possible to implement the embodiment comprising the inner and outer ring members without a spring member. The user may then for instance move the adjustment ring between the locked and unlocked positions in a separate action from the adjustment action.

According to a further preferred embodiment, the adjustment mechanism and the adjustment ring comprise at least one cooperating groove-notch mechanism comprising at least one groove and one corresponding notch. The mechanism is preferably arranged such that rotation of the adjustment ring is impossible, as such prevented, when the notch is received in the groove. The adjustment mechanism may be provided with a plurality of grooves and possibly also a plurality of notches.

Preferably, the spring member is arranged to urge the notch in the groove upon rotational alignment of the notch and the groove. As an alternative, as mentioned above, the configuration using the notch-groove mechanism may be applied without any spring member.

When the adjustment ring is movable between a locked and unlocked position along the adjustment axis as described above, it is preferred if the adjustment mechanism is arranged to disengage the notch from the groove when the adjustment ring is moved along the adjustment axis from the locked to the unlocked position. Movement of the adjustment ring will then disengage the notch from the groove, thereby allowing rotation of the ring and thus adjustment of e.g. the length of the adjustment device. It is possible that the notch is urged in the groove, upon alignment, by a spring member, such that the spring force needs to be overcome before moving the notch out of the groove, thereby allowing rotation of the adjustment ring.

The adjustment ring can be positioned in the unlocked position upon exertion of an axial force, for instance along the adjustment axis. After release of said force, the position of the adjustment ring is changed to the locked position when the notch is aligned with the groove.

Preferably, the adjustment mechanism comprises a plurality of notches and/or grooves. It is not required that the number of notches corresponds to the number of grooves, e.g. in order to establish the option for a specific incremental adjustment. In a preferred embodiment, the number of notches and grooves is chosen equally, corresponding to an incremental change relevant for user-friendly clinical application, e.g. alignment every half or full turn of the adjustment ring.

A compact and intuitive adjustment mechanism is obtained when the adjustment ring comprises a notch protruding from its lower surface. The notch can then be received in a groove of the tubular base body or any member opposite the lower surface of the ring. As an alternative, the lower surface of the ring is provided with a groove cooperating with a notch extending from a surface opposite the lower surface of the ring. Moving the ring relative to the tubular base body or other member will then disengage the notch from the groove, thereby allowing rotation. When using an adjustment ring comprising an inner and an outer ring, it is preferred when the outer ring member is provided with a notch.

According to a further preferred embodiment, the adjustment mechanism, for instance the spring member thereof, is arranged to bias rotation of the adjustment ring such that the force, or the number of actions, required for rotation in a first rotation direction is larger than the force, or the number of actions, required for rotation in the opposite direction. In other words, rotating the ring in the first direction takes more force or actions than rotating in the second, opposite direction. Preferably, the adjustment mechanism is arranged such that upon movement in the second direction, the extension tube is extended from the base body. Accidentally rotating the adjustment ring in the first direction, thereby shortening the distance between the bone parts, is then prevented.

Preferably the groove-notch mechanism hereto has an asymmetric configuration, wherein the shape of the groove and/or the notch in a first rotation direction of the adjustment ring is different from the shape of the groove and/or the notch in the opposite rotation direction of the adjustment ring. Movement of the notch out of the groove is then more difficult or even impossible when rotating the ring in the first direction than when rotating the ring in the second direction.

Preferably, the groove is U- or V-shaped, having a base and two sidewalls extending therefrom, wherein the angles of the two sidewalls are different. The first sidewall of the groove may make a relative large angle with respect to the base (or relative to the direction of rotation) such as 70-90 degrees, possibly even 90 degrees. The first sidewall is then substantially perpendicular to the rotation direction, such that rotation is hardly possible without first moving the notch out of the groove in a separate action, for instance by axially moving the adjustment ring. The second sidewall of the groove may make a smaller angle with respect to the base (or relative to the direction of rotation), for instance between 20-60 degrees, preferably between 40 and 50 degrees. Upon rotation of the notch towards this sidewall, the angled sidewall will urge the notch out of the groove, thereby making it easier to rotate in the preferred operating direction. Moving the adjustment mechanism towards the unlocked position is then easier when rotating in the second direction. It is also possible that the notch has a U- or V-shape having the different sidewalls. Preferably, the shapes of the notch and groove correspond.

According to a further preferred embodiment, the extension tube comprises an inner tube and an outer tube movable with respect to the inner tube, wherein the adjustment mechanism is arranged to move the outer sheath with respect to the base body, wherein the extension tube further comprises a damping and/or resiliency mechanism, for instance a spring member. The mechanism may be arranged for damping the relative movement of the inner tube and the outer sheath. A damping mechanism and/or resiliency between the first and second connection devices may improve the distraction process.

The invention further relates to an adjustment device or mechanism as such as described above, in particular for use in an external distractor as described above.

The present invention is further illustrated by the following Figures, which show a preferred embodiment of the device according to the invention, and are not intended to limit the scope of the invention in any way, wherein:

FIG. 1 schematically shows an external distractor including an adjustment mechanism;

FIGS. 2a and 2b schematically show the adjustment device in a locked position in perspective view and cross-sectional view, respectively;

FIGS. 3a and 3b schematically show the adjustment device in an unlocked position in perspective view and cross-sectional view, respectively;

Figure 1:
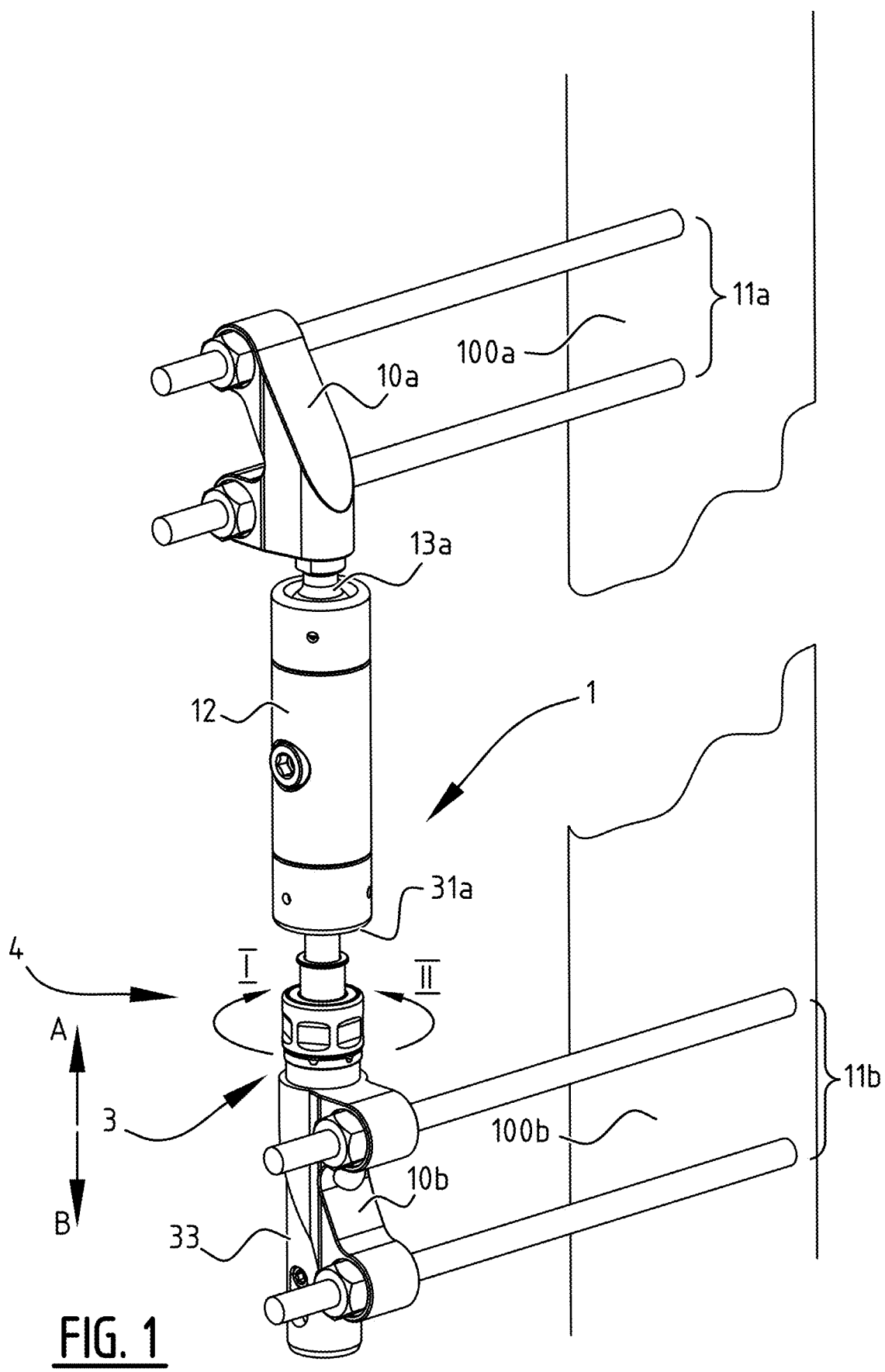

In FIG. 1, an external distractor 1 is shown which is arranged to enlarge the distance between a first bone, schematically indicated with 100a, and second bone, schematically indicated with 100b. The external distractor comprises a first connection device 10a and a second connection device 10b at a mutual distance from each other. The first connection device 10a is coupled to the first bone part 100a with two bone pins, which can be one or more bone pins in other preferred embodiments, 11a and the second connection device 10b connected to the second bone part 100b with two bone pins 11b. Coupled between the two connection devices is a connection element 12 which is provided with two receptacles at its end to receive two balls 13a and 31a (see also FIGS. 2 and 3) to form two ball joints. The distractor further comprises an adjustment device 3 coupled to a second connection device 10b for adjusting the distance between the first and the second connection devices 10a, 10b along an adjustment axis A,B. The adjustment device 3 is coupled to the rod 12 in this example. The adjustment device 3 comprises a tubular base body 33, which is coupled to the second connection device 10b. The adjustment device 3 further comprises an extension tube 31 which is movable with respect to the base body 33 along the adjustment axis A,B. At the end of extension tube 31, the ball 31a is provided. The extension tube 31 is movable in a telescopic manner with respect to the base body 33 under the influence of an adjustment mechanism 4, in this example a rotatable adjustment ring 4. Rotation of the ring (indicated with arrows I and II) will result in extension (indicated with arrow A) or withdrawal (indicated with arrow B) of the extension tube 31 with respect to the base body 33. Such a device is known from WO2017/016611 A1, which is hereby incorporated by reference.

To prevent unintended rotation of the ring 4, and thus intentional activation of the adjustment mechanism 4, the lower surface 49 of the ring 4 (see also FIG. 4), is provided with a notch 44 protruding from the lower surface 49 of the ring 4. An upper surface 33a of the base body 33 is provided with one or more (in this example two) correspondingly shaped grooves 34. In fact, the upper surface 33a is provided with two grooves 34 (see again FIG. 4), while also the ring 4 is provided with two notches or protrusions 44 (one visible). The notches and grooves are provided at mutual the same distances, such that the notches and grooves fit at different positions of the ring 4 with respect to the base body 33.

Figure 2A:
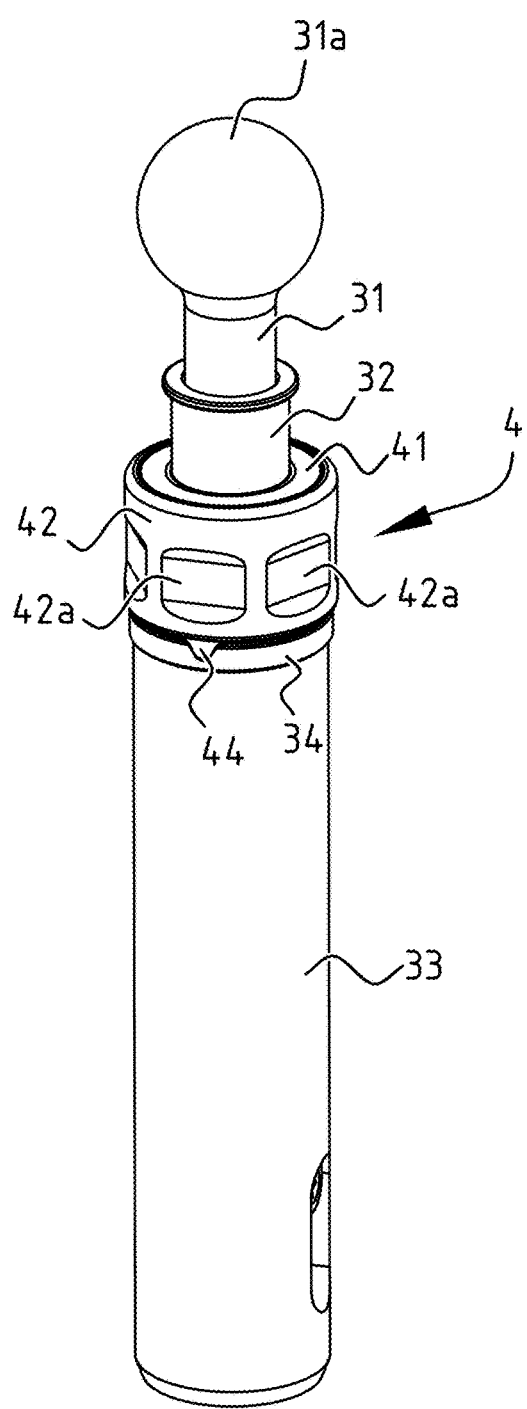
Figure 2B:
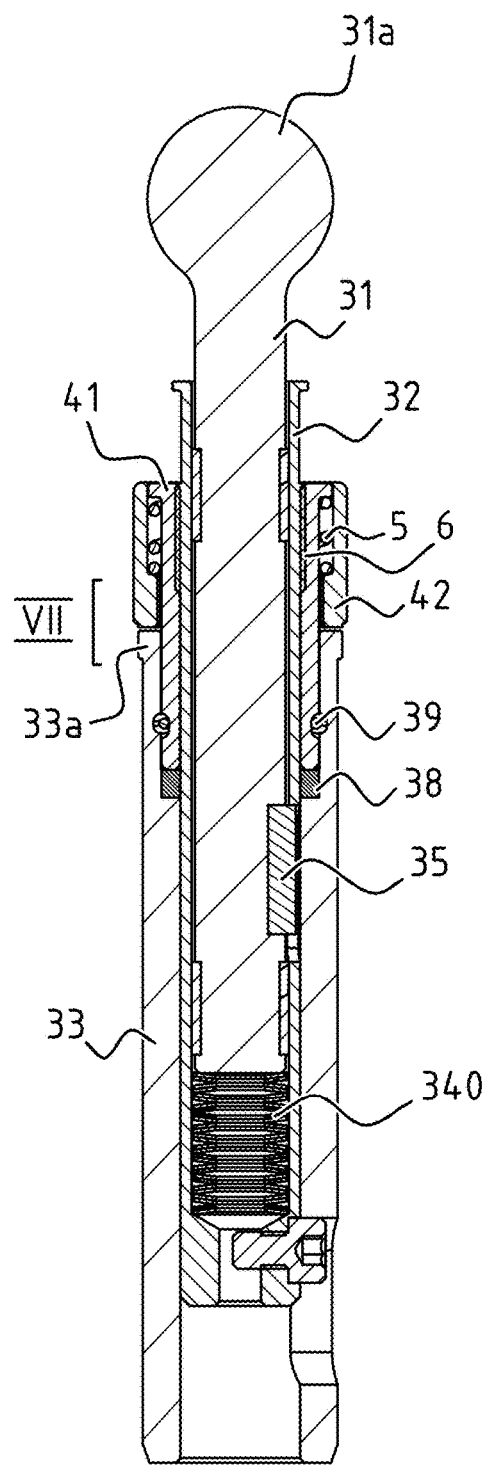
Figure 3A:
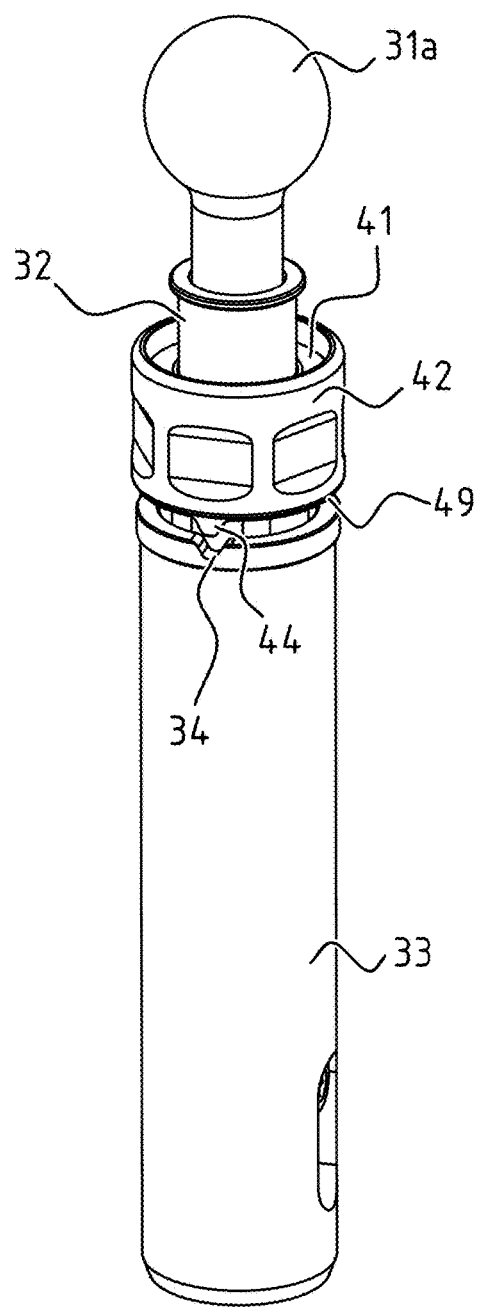
Figure 3B:
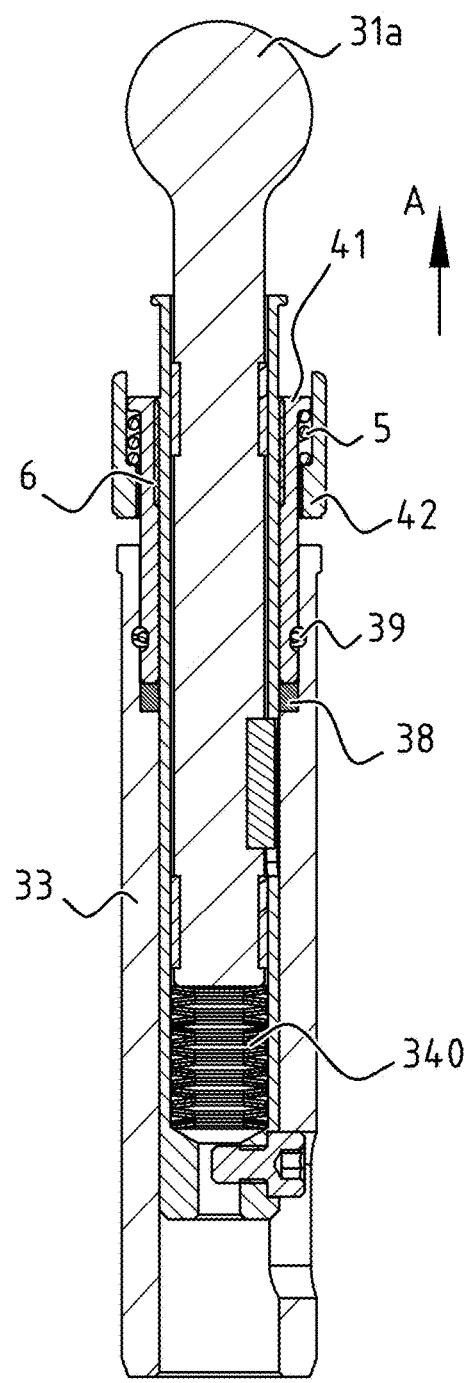

In the position as shown in FIGS. 2A and 2B, which will also be referred to as the locked position, the notch 44 is received in the groove 34, such that rotation of the ring 4 with respect to the base body 33 is difficult. The notch 44 and the groove 34 are arranged to prevent rotation, at least rotation without any movement of the ring 4 in an upwardly direction A as will be explained below. That is, when the ring 4, specifically an outer part 42 thereof, is moved upwardly in a direction A as shown in FIGS. 3A and 3B, the notch 44 comes free from the groove 34, such that rotation is possible.

As said, in this example the ring 4 comprises an outer ring 42 and an inner ring 41, wherein the outer ring 42 is axially (indicated with arrow A) movable with respect to the inner ring 41. The inner ring 41 is fixed, in the axial direction, to the base body 33, in this example using a ring 39 received in grooves provided in the inner ring 41 and the inner surface of the base body 33. Inner ring 41 is however rotatable within the tubular base body 33. A bushing 38 facilitates the rotation.

Figure 4:
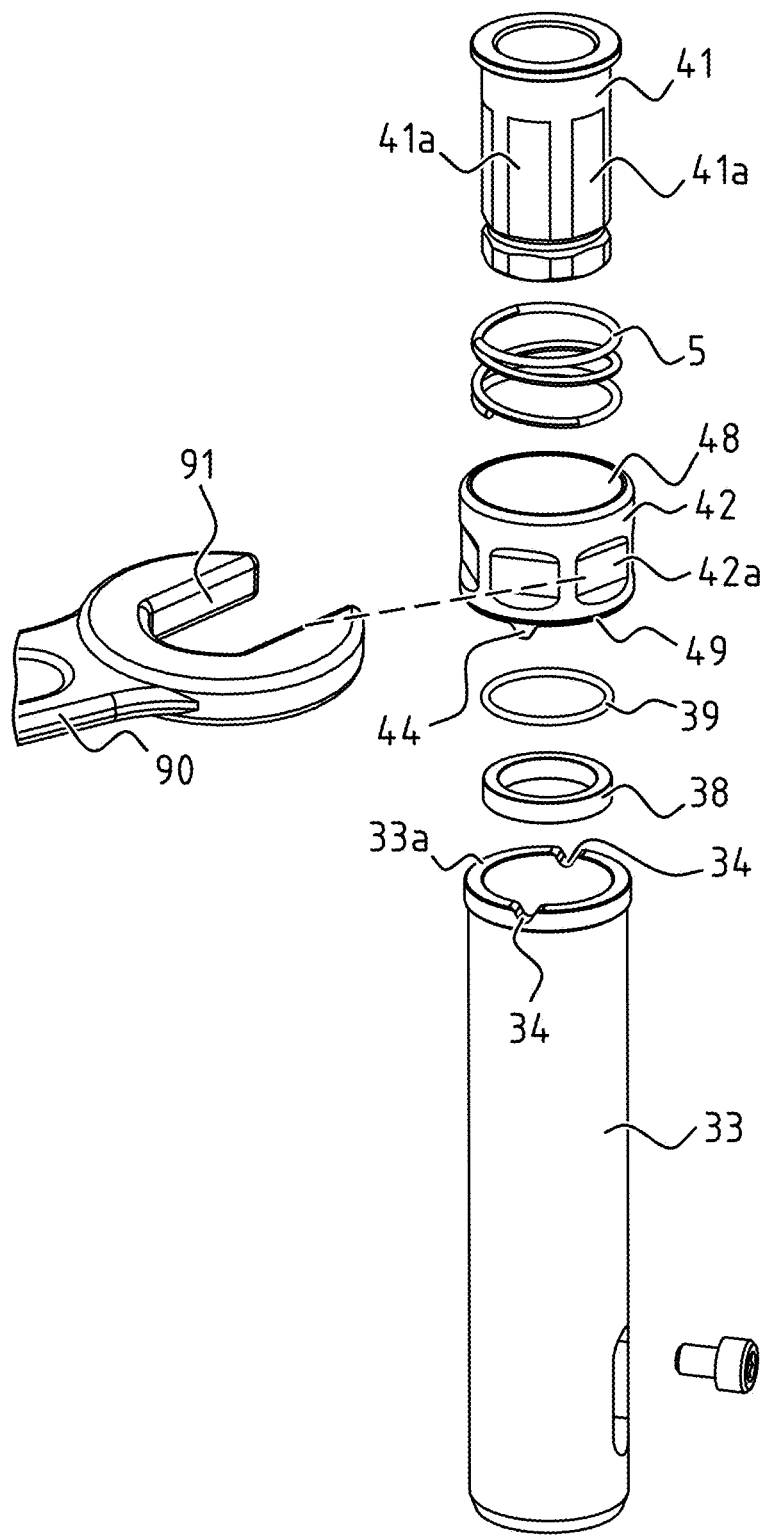
FIG. 4 shows the adjustment device in exploded view.

With specific reference to FIG. 4, it can be seen that the outer surface 41a of the inner ring 41 is non-cylindrical. The inner surface of the outer ring 42 has a corresponding, that is complementary shaped, inner surface 48 (not visible), similar to the flat surfaces 42a at the outside. Rotation of the outer ring 42, when possible, will thus result in rotation of the inner ring 41 due to engagement of outer surface 41a of the inner ring 41 and the inner surface 48 of the outer ring 42. Another mechanism for coupling the inner and outer rings in a rotating manner may be provided, for instance by a cam received in a groove. The inner ring 41 and the outer ring 42 are preferably coupled in a manner such that relative rotation is not possible (rotationally fixed, FIG. 1I-II), while axial movement is possible (axially movable, FIG. 1A-B).

The inner tube 41 and the extension tube 31, in particular an outer tube 32 thereof, are provided with cooperating threading 6. Rotation of the inner ring 41, due to rotation of the outer ring 42, will thus result in axial movement of the outer tube 32 with respect to the base body 33. In this example, the extension tube 31 and the outer tube 32 are relatively movable with respect to each other under the influence of a spring 340. This provides resiliency during the distraction process. Tubes 31 and 32 are only axially movable. Mutual rotation is prevented using cam 35.

Thus, for extending or withdrawing the extension tube 31 with respect to the base body 33, the outer ring 42 needs to be moved upwardly from the locked position (FIGS. 2A and 2B) towards the unlocked position (FIGS. 3A and 3B). The notch 44 is then free from the groove 34, such that the ring 4 can be rotated, thereby axially moving the extension tube 31. Moving the outer ring 42 downwardly will again lock the adjustment mechanism 4 upon re-alignment of notch 44 and groove 34.

To prevent accidental movement of the adjustment mechanism to the unlocked position, and thus to prevent rotation and activation of the adjustment mechanism, a spring member 5 is provided between the inner ring 41 and the outer ring 42 which urges the outer ring downwardly, i.e. towards the locked position. When the user releases the outer ring and the notches and the grooves are aligned, the notch 44 will fit in groove 34, thereby locking the adjustment mechanism. When the notch 44 is not aligned with groove 34, the user needs to rotate further until the outer ring 42 is aligned. The notch-groove mechanism 33, 44 hereby functions as guidance for the amount of extension.

The spring member 5 not only functions to move the outer ring 42 downwardly again after use, it also prevents accidental rotation. As said, the outer ring 42 is only rotatable when moved upwardly. The spring member 5 acts against this movement, such that the user needs to counter the force of the spring member.

Figure 5A:
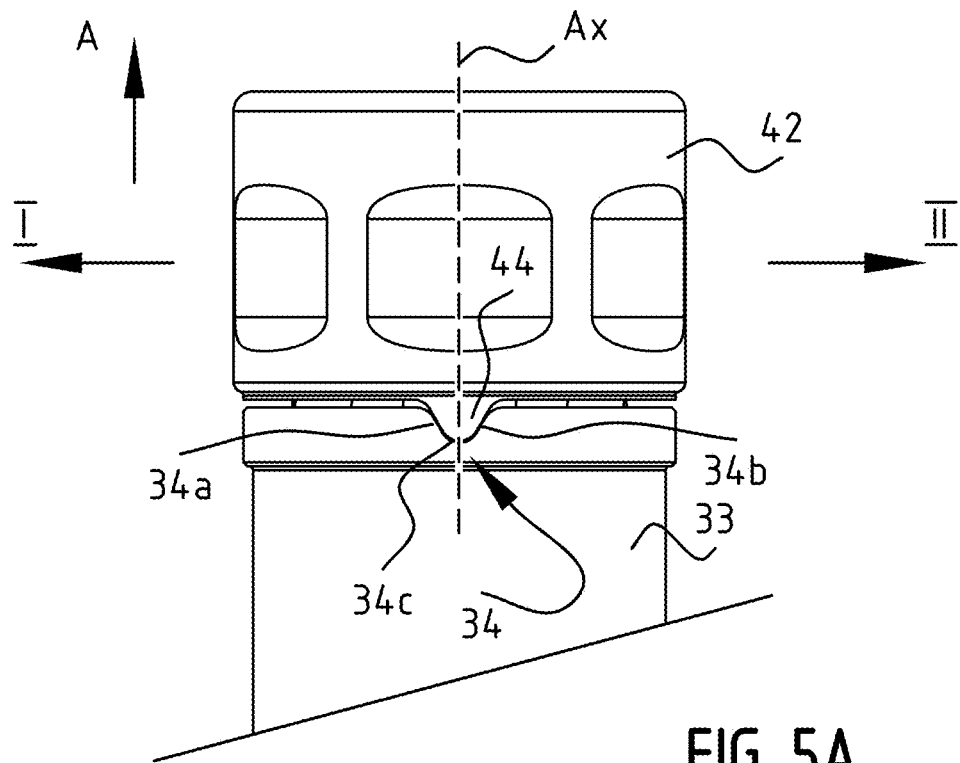
FIGS. 5a and 5b show two embodiments of a notch-groove mechanism as part of an adjustment mechanism.

In the detail of FIG. 5a it is visible that the groove 34 and the notch 44 have a V-shape, having a bottom 34c and two sidewalls 34a, 34b extending therefrom. In the example of FIG. 5a, the sidewalls 34a, b are shaped symmetrically with respect to an axis AX through the base 34c and which is perpendicular to the direction I, II of rotation. The sidewalls 34a, 34b make an angle of approximately 45 degrees with respect to the bottom of the base 34c. Rotation in a direction I or II will under the influence of the shape of the sidewalls thus result in a movement upwardly (indicated with A). In other words, the coopering sidewalls of the notch 44 and the groove 34 will urge the outer ring 42 upwardly upon rotation of outer ring 4. Any spring member 5 counters this movement. Rotating of the ring 4 can be done manually. In an alternative, a tool 90 can be used, which is arranged to engage the surfaces 42a of the ring (see FIG. 4). The tool 90 may be provided with a correspondingly shaped engagement surface 91.

Figure 5B:
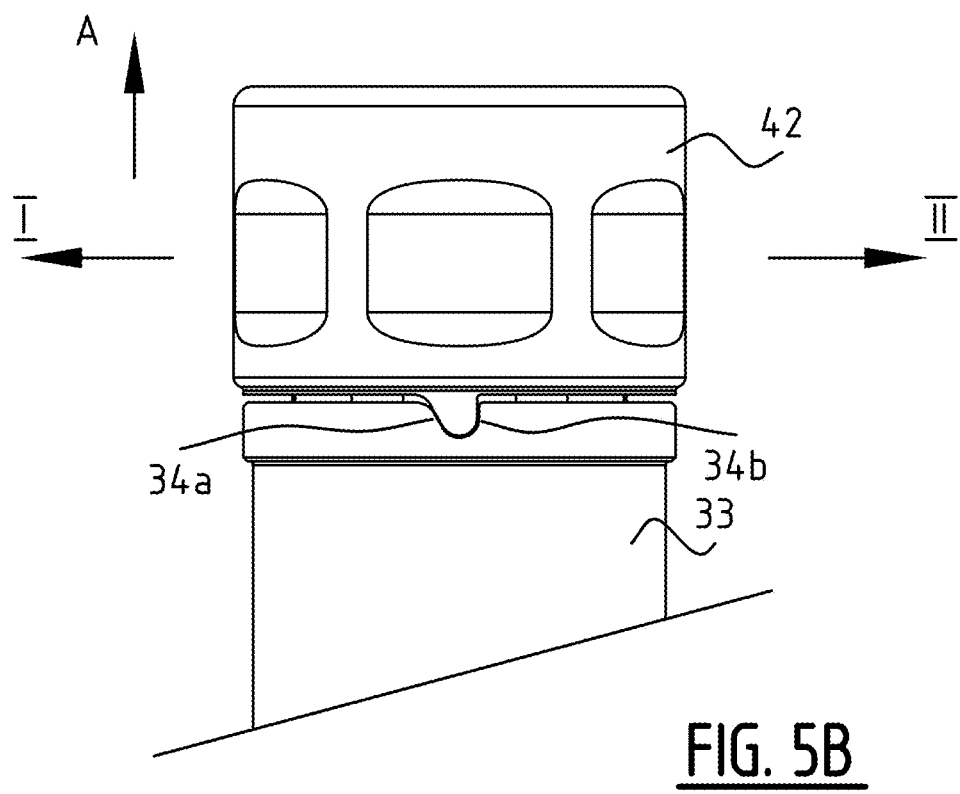

In the example of FIG. 5b, the sidewalls 34a, 34b are shaped asymmetrically. Sidewall 34a has a configuration similar to the sidewall 34a of FIG. 5a, while the other sidewall 34b is perpendicular to the direction of rotation I, II, parallel to axis AX. A movement of the ring 42 in a direction II with respect to the base body 33 will thus not lead to upwardly urging as will be case when the ring 42 will be rotated in the direction I. For rotation in the direction II, the ring 42 needs to actively lifted for freeing the notch 44 from the groove 34, while when rotating in the direction I, the cooperating sidewalls 34a will urge the ring 42 upwardly. Accidental rotation in the direction II is thus prevented.

Figure 6A:
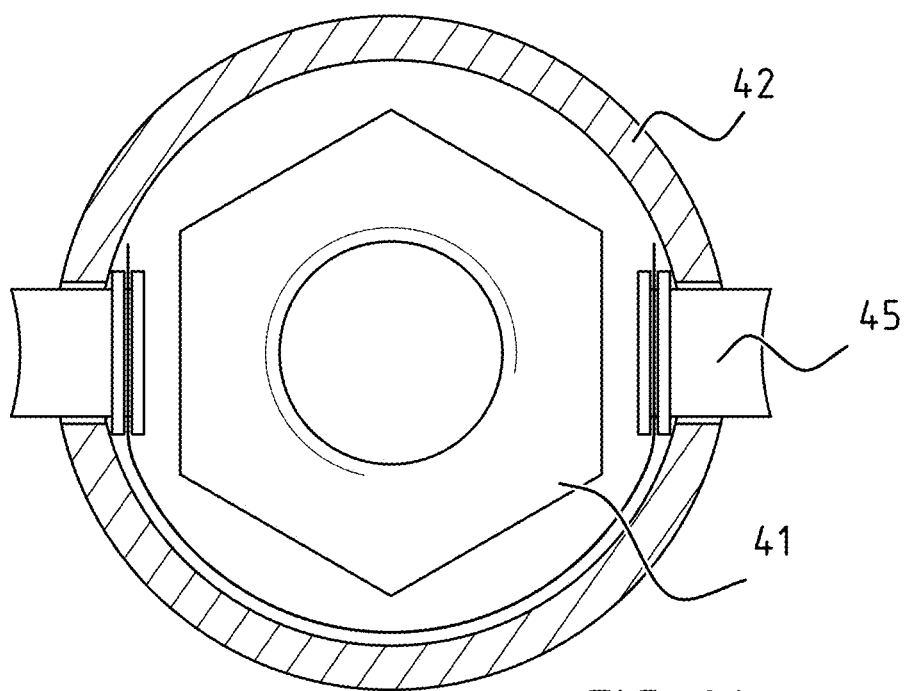
FIGS. 6a and 6b show an alternative adjustment mechanism, in disengaged and engaged position, respectively.
Figure 6B:
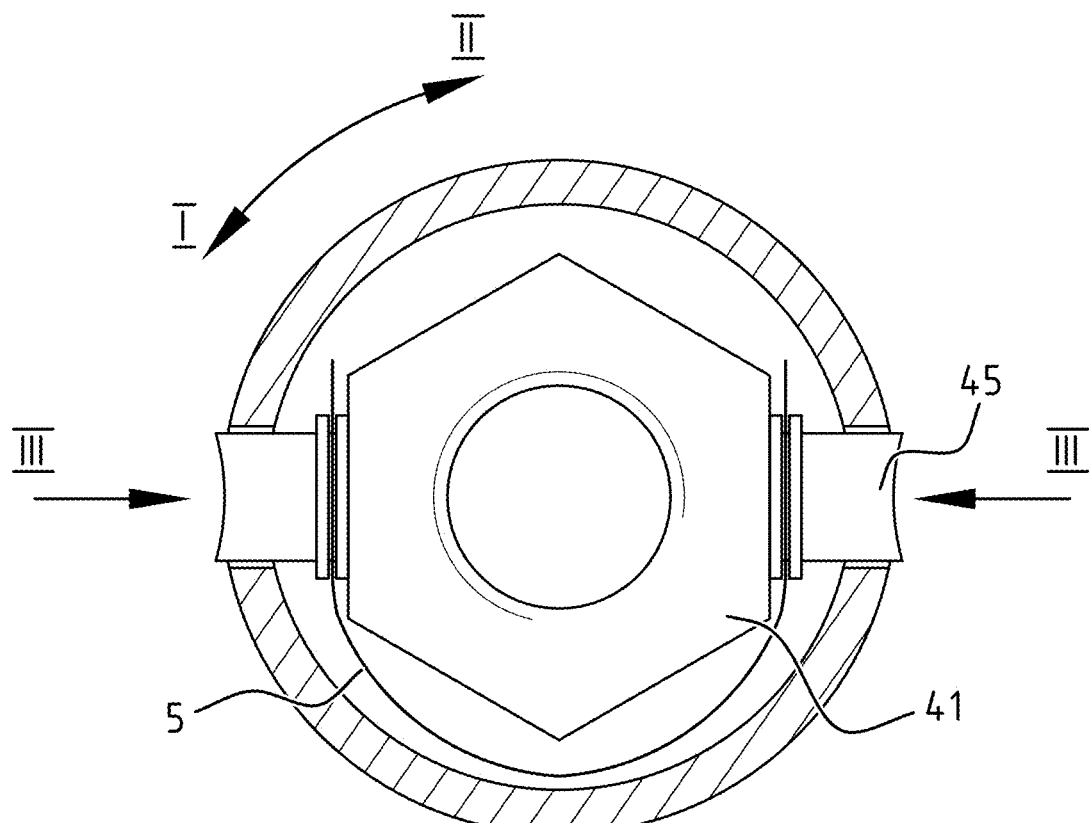

FIGS. 6A and 6B show an alternative adjustment mechanism. Outer ring 42 is freely rotatable with respect to inner ring 41. However, only when tabs 45 are moved inwardly (see direction indicated with arrows III in FIG. 6B, the tabs 45 are coupled to the outer ring 42 and will engage the inner ring 41, thereby imparting any rotation of the outer ring 42 to the inner ring 41. A spring member 5 is provided to urge the tabs 45 towards the disengaged position (FIG. 6A) and prevent any unintended movement of the tabs 45, or generally activation of the adjustment mechanism, from the disengaged position (FIG. 6A) towards the engaged position (FIG. 6B). In this example, two tabs 45 are provided which can be actuated with e.g. two fingers or an additional tool 90. Additional tabs may be provided, making it more difficult, if not impossible, to manually activate the adjustment mechanism, such that an additional tool 90 (see FIG. 4) may be required.

Figure 7A:
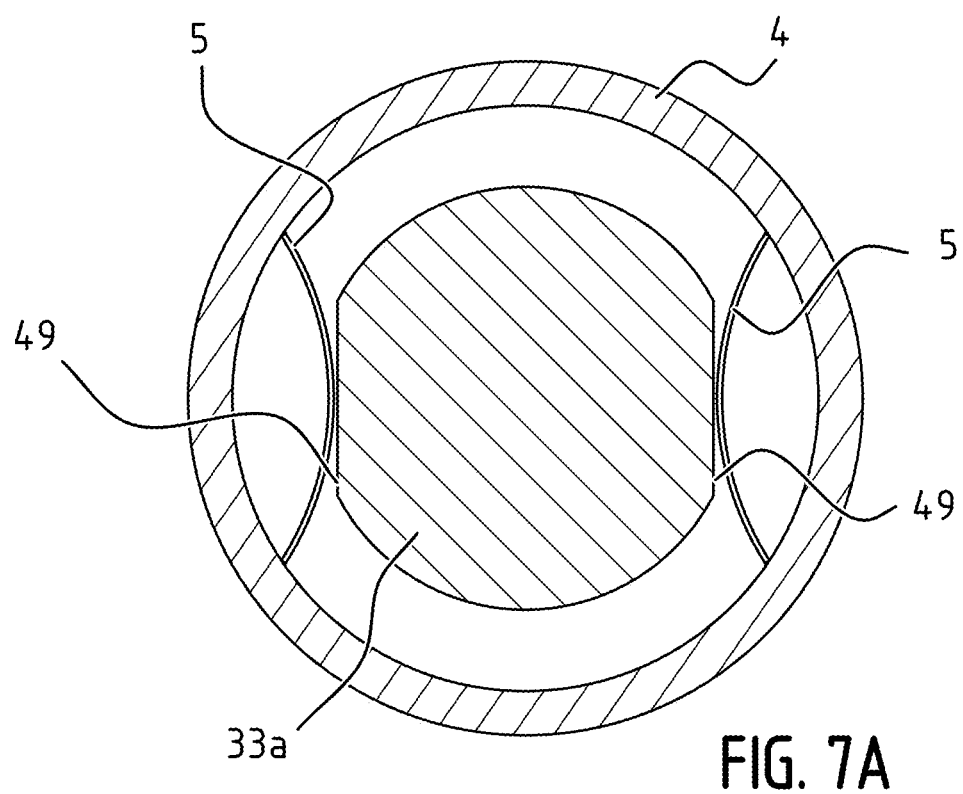
FIGS. 7a and 7b show a further alternative adjustment mechanism, in locked and unlocked position, respectively.
Figure 7B:
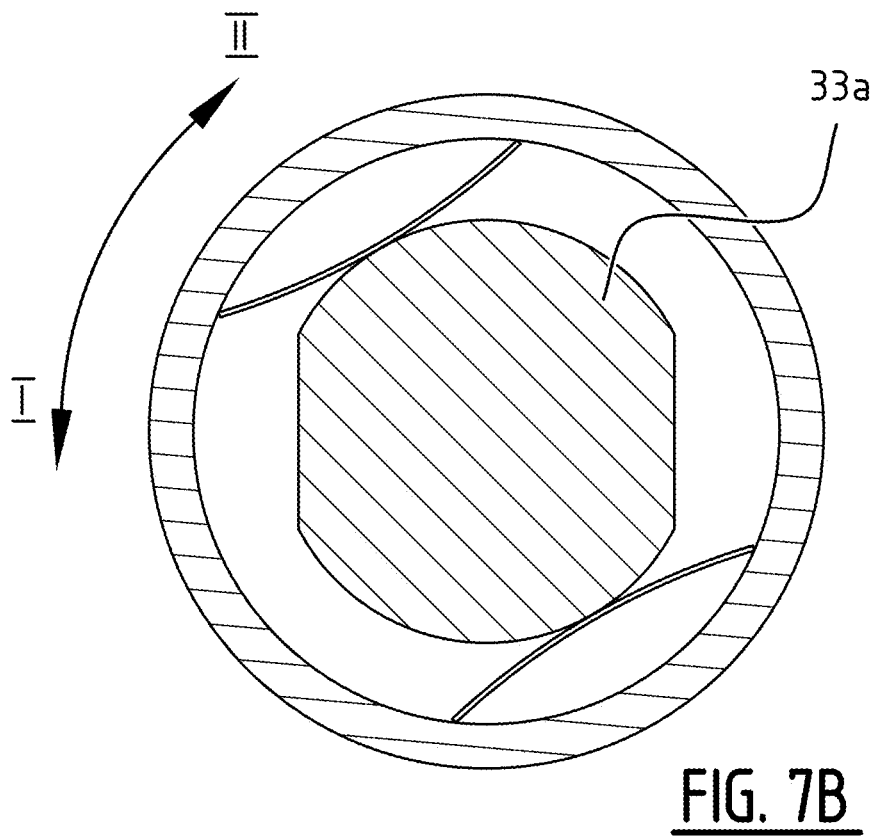

The example of FIGS. 7A and 7B show an alternative to prevent accidental rotation of the ring 4 with respect to the base body 33, for instance an upper part 33a thereof (see the indication VII in FIG. 2B for an idea of the location of the mechanism of FIGS. 7A and 7B). The ring 4 is freely rotatable with respect to the base body 33, with the exception of the spring members 5 engaging the ring 42. In locked position (FIG. 7A), the spring members 5 engage spring surfaces 49, such that rotation is only possible when the spring force is overcome. This is shown in FIG. 7B. The ring 4 may be provided with threading for directly cooperating with the extension tube 32.

Figure 8A:
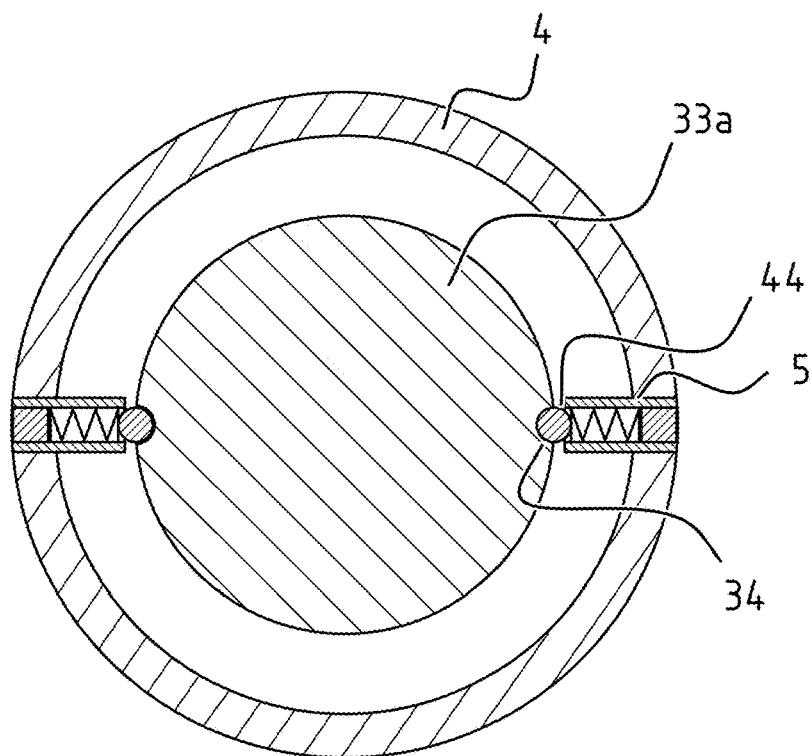
FIGS. 8a and 8b show a further alternative adjustment mechanism, in locked and unlocked position, respectively.
Figure 8B:
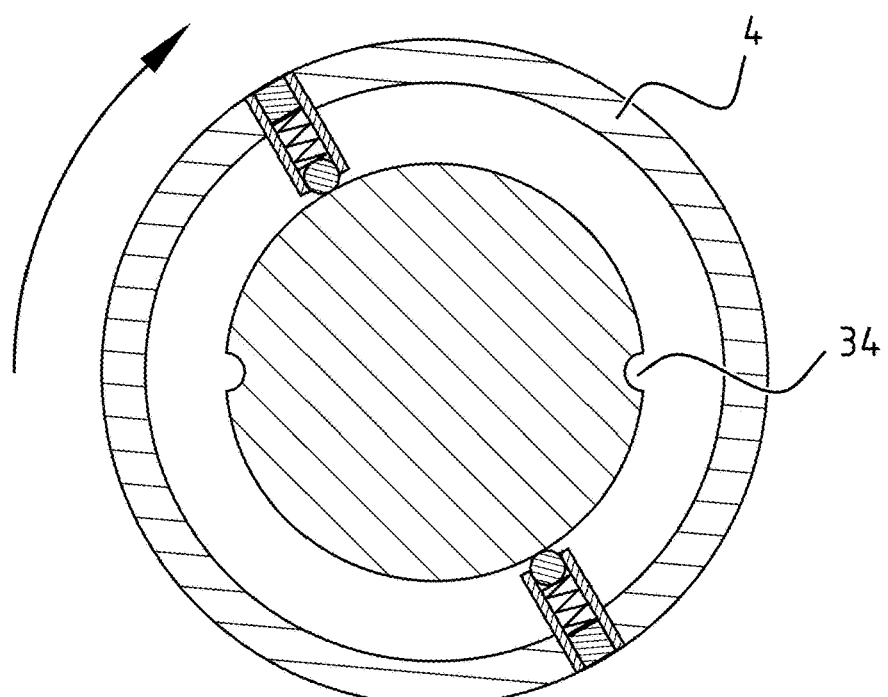

FIGS. 8A and 8B show another example of a spring member based mechanism to prevent accidental rotation. Adjustment ring 4 is provided with spring loaded protrusions 44 (see spring members 5) which engage grooves 44 in the base body 33, for instance again the upper part 33a thereof. Only when sufficient torque is provided, the notches 44 will snap out of the grooves 34, thereby allowing rotation (see FIG. 8B). Also here, the grooves 34 and/or notches 44 could be formed asymmetrical. Upon rotating, the notches 44 will again snap back into grooves 34 when properly aligned. Also this system, as the previous systems, this forces the user to rotate the ring 4 with predetermined rotational distances.

The present invention is not limited to the embodiments shown, but extends also to other embodiments falling within the scope of the appended claims.

The invention claimed is:

1. An external distractor arranged to gradually enlarge the distance between a first bone part and a second bone part, wherein the distractor comprises:
   a first and a second connection device, wherein the first connection device is arranged to be connected to the first bone part with at least one first bone pin and wherein the second connection device is arranged to be connected to the second bone part with at least one second bone pin,
   wherein the distractor further comprises an adjustment device arranged between the first and second connection devices for adjusting the distance between the first and the second connection devices along an adjustment axis, wherein the adjustment device comprises a tubular base body coupled to the first connection device, an extension tube coupled to the second connection device and an adjustment mechanism for moving the extension tube with respect to the base body along the adjustment axis, wherein the adjustment mechanism comprises a rotatable adjustment ring for moving the extension tube upon rotation of the adjustment ring around the adjustment axis, wherein the adjustment mechanism further comprises at least one spring member engaging the adjustment ring for preventing unintended activation of the adjustment mechanism, wherein the adjustment ring is movable between a locked position, in which rotation of the ring is prevented, and an unlocked position in which the ring is rotatable, and wherein the spring member is arranged to urge the adjustment ring towards the locked position, wherein the adjustment ring is movable along the adjustment axis between the locked and unlocked positions, and wherein the adjustment ring and the base body of the adjustment device comprise a cooperating groove-notch mechanism comprising at least one groove and one corresponding notch, wherein rotation of the adjustment ring is prevented when the notch is received in the groove.

2. The external distractor according to claim 1, wherein the spring member is arranged to prevent unintended rotation of the adjustment ring.

3. The external distractor according to claim 1, wherein the adjustment ring comprises an inner ring member and an outer ring member, wherein the outer ring member is arranged to be engaged by a user, wherein the inner ring member and outer ring member are coupled in a substantially form locked manner such that rotation of the outer ring member rotates the inner ring member, and wherein the outer ring member is movable with respect to the inner ring member along the adjustment axis.

4. The external distractor according to claim 3, wherein the inner ring member and the extension tube are provided with cooperating threading for moving the extension tube upon rotation of the inner ring.

5. The external distractor according to claim 4, wherein the spring member is arranged between the inner and outer ring member.

6. The external distractor according to claim 3, wherein the outer ring member is provided with a notch.

7. The external distractor according to claim 1, wherein the spring member is arranged to urge the notch in the groove upon alignment of the notch and the groove.

8. The external distractor according to claim 1, wherein the adjustment mechanism is arranged to disengage the notch from the groove when moving the adjustment ring along the adjustment axis from the locked to the unlocked position.

9. The external distractor according to claim 1, wherein the groove-notch mechanism has an asymmetric configuration, and wherein the shape of the groove and/or the notch in a first rotation direction of the adjustment ring is different from the shape of the groove and/or the notch in the opposite rotation direction of the adjustment ring.

10. The external distractor according to claim 9, wherein the groove and/or notch is U- or V-shaped, having a base and two sidewalls extending therefrom, and wherein the angles of the two sidewalls are different.

11. The external distractor according to claim 1, wherein the adjustment ring comprises a notch protruding from its lower surface.

12. The external distractor according to claim 1, wherein the adjustment mechanism comprises a plurality of notches and/or grooves.

13. The external distractor according to claim 1, wherein the extension tube comprises an inner tube and an outer tube movable with respect to the inner tube, wherein the adjustment mechanism is arranged to move the outer tube with respect to the base body, and wherein the extension tube further comprises a damping mechanism for damping the relative movement of the inner tube and the outer tube.

14. The external distractor according to claim 1, the adjustment mechanism is configured to receive a tool for engaging and operating the adjustment mechanism.

15. The external distractor according to claim 1, wherein the spring member is arranged to increase the rotational force needed to rotate the ring to such an extent that manually operating the ring is not possible.

16. A combination of an external distractor according to claim 15 and a tool cooperating with the ring for rotating said ring.

17. An adjustment device for use in an external distractor, the adjustment device comprising:
a tubular base body coupled to a first connection device;
an extension tube coupled to a second connection device; and
an adjustment mechanism for moving the extension tube with respect to the base body along an adjustment axis,
wherein the adjustment mechanism comprises a rotatable adjustment ring for moving the extension tube upon rotation of the adjustment ring around the adjustment axis,
wherein the adjustment mechanism further comprises at least one spring member engaging the adjustment ring for preventing unintended activation of the adjustment mechanism, wherein the adjustment ring is movable between a locked position, in which rotation of the ring is prevented, and an unlocked position in which the ring is rotatable, and wherein the spring member is arranged to urge the adjustment ring towards the locked position, wherein the adjustment ring is movable along the adjustment axis between the locked and unlocked positions, and
wherein the adjustment ring and the base body of the adjustment device comprise a cooperating groove-notch mechanism comprising at least one groove and one corresponding notch, wherein rotation of the adjustment ring is prevented when the notch is received in the groove.

* * * * *

UNITED STATES PATENT AND TRADEMARK OFFICE
CERTIFICATE OF CORRECTION

PATENT NO.           : 12,310,626 B2                         Page 1 of 1
APPLICATION NO.      : 17/638032
DATED                : May 27, 2025
INVENTOR(S)          : Thijmen Struik et al.

It is certified that error appears in the above-identified patent and that said Letters Patent is hereby corrected as shown below:

On the Title Page

Item (72) Inventors, "Karianne Hide Lindenhovius" should be --Karianne Hilde Lindenhovius--.

Signed and Sealed this
Fifteenth Day of July, 2025

Coke Morgan Stewart
*Acting Director of the United States Patent and Trademark Office*